United States Patent [19]
Manz et al.

[11] Patent Number: 5,158,747
[45] Date of Patent: Oct. 27, 1992

[54] APPARATUS FOR IDENTIFYING AND DISTINGUISHING DIFFERENT REFRIGERANTS

[75] Inventors: Kenneth W. Manz, Paulding; Gary P. Murray, Montpelier, both of Ohio; Charles E. Dull, Fort Wayne, Ind.

[73] Assignee: SPX Corporation, Muskegon, Mich.

[21] Appl. No.: 692,184

[22] Filed: Apr. 26, 1991

[51] Int. Cl.$^5$ .................... G01N 7/00; G01N 27/00
[52] U.S. Cl. ..................................... 422/98; 422/83; 73/24.04; 73/25.04; 73/29.03; 62/125; 62/127
[58] Field of Search .................. 422/83, 98; 73/25.01, 73/25.04, 24.01, 24.04, 29.01, 29.03; 324/663; 435/3, 289, 807; 62/125, 127, 129

[56] References Cited

U.S. PATENT DOCUMENTS

| | | | |
|---|---|---|---|
| 3,264,862 | 8/1966 | Felton et al. | 73/25.01 |
| 3,535,915 | 10/1970 | Felton et al. | 73/25.01 |
| 3,544,276 | 12/1970 | Merwitz | 62/125 |
| 4,530,233 | 7/1985 | Kadi | 62/125 |
| 4,679,947 | 7/1987 | Miller et al. | 73/24.04 |
| 4,768,347 | 9/1988 | Manz et al. | 62/149 |
| 4,805,416 | 2/1989 | Manz et al. | 62/292 |
| 4,849,988 | 7/1989 | Chien | 73/29.01 |
| 4,878,356 | 11/1989 | Punches et al. | 62/149 |
| 4,939,905 | 7/1990 | Manz | 62/77 |

Primary Examiner—Robert J. Warden
Assistant Examiner—T. A. Trembley
Attorney, Agent, or Firm—Barnes, Kisselle, Raisch, Choate, Whittemore & Hulbert

[57] ABSTRACT

Apparatus for identifying and distinguishing between at least two different types of refrigerant includes a sample container having a fixed internal volume. Refrigerant to be tested is selectively admitted into the container in vapor phase, vapor pressure of refrigerant within the container is measured, and admission of refrigerant into the container is terminated when the vapor pressure of refrigerant contained therein reaches a preselected level. A sensor and associated electronics are coupled to the container for determining type of refrigerant vapor in the container as a function of one or more selected properties of the refrigerant, and indicating such refrigerant type to the operator.

26 Claims, 2 Drawing Sheets

APPARATUS FOR IDENTIFYING AND DISTINGUISHING DIFFERENT REFRIGERANTS

The present invention is directed to refrigerant handling systems such as air conditioners and heat pumps, and more particularly to apparatus for identifying and distinguishing differing types of refrigerants for service of such systems.

BACKGROUND AND OBJECTS OF THE INVENTION

It is now widely recognized and accepted that release into the atmosphere of chlorofluorocarbon(CFC)-based refrigerants, such as refrigerant R12, has a deleterious effect upon the ozone layer that surrounds the earth. Production of CFC-based refrigerants may be severely curtailed in the future, and the cost of refrigerant for service purposes is already increasing. It is therefore becoming standard practice in the refrigerant system service industry to recover, purify and reuse refrigerant in a refrigeration system under service, rather than merely to vent such refrigerant into the atmosphere and replace with new refrigerant, as had been common practice in the past. U.S. Pat. Nos. 4,768,347, 4,805,416 and 4,878,356, all assigned to the assignee hereof, disclose equipment for recovering, purifying and/or recharging refrigerant in a refrigeration system service environment.

As currently envisioned, R12 refrigerant will eventually be replaced by different types of refrigerants in production of new refrigeration systems. For example, R12 refrigerant may be replaced by R134a refrigerant in the automotive industry—i.e., in automotive air conditioning systems. However, because these refrigerants and their associated lubricants are chemically incompatible with each other, inadvertent mixture of even a small amount of the differing refrigerants can cause severe damage and early failure of the refrigeration system. It has been proposed to provide different service fittings on refrigeration equipment using different types of refrigerants, but the use of adaptors and the like in the service industry may still result in inadvertent mixing of refrigerant/lubricant types, with consequent damage to the system under service or to the service equipment itself.

A further complication arises with the use of intermediate refrigerants as substitutes for R12 refrigerant, such as ternary blends made by DuPont. With severe curtailment of R12 production that may take place, it is anticipated that a significant number of refrigeration systems currently employing R12 refrigerant may eventually be retrofitted with an intermediate substitute refrigerant. Inadvertent mixing of refrigerants is considered to be an irreversible process, leading to disposal of the mixed refrigerant as hazardous waste. U.S. Pat. No. 4,939,905, assigned to the assignee hereof, discloses a refrigerant recovery system that includes a recovery compressor, a multiple-section condenser and means for automatically distinguishing between R12, R22 and R502 refrigerants at the compressor inlet, as a function of refrigerant vapor pressure and temperature, and switching the compressor outlet among the condenser sections to prevent mixing of refrigerants in the condenser. However, the temperature/saturation pressure characteristics of R12, R134a and blend refrigerants are such that these refrigerants cannot as readily be distinguished as a function of these characteristics.

There is therefore a need in the refrigeration system service industry for a device that can be employed to test refrigerant in a storage container or in a refrigeration system before performing service on the system, that is not restricted to any particular type of refrigerant or to automotive service applications, that is particularly well adapted to identify and distinguish between refrigerants of different types, that is inexpensive to manufacture and market, that is readily portable, that is rapid and efficient in operation, and/or that can be employed by relatively untrained service personnel. It is a general object of the present invention to provide such a device.

SUMMARY OF THE INVENTION

Apparatus for identifying and distinguishing between at least two different types of refrigerant in accordance with the present invention includes a sample container having a fixed internal volume. Refrigerant to be tested is selectively admitted into the container, vapor pressure of refrigerant within the container is measured, and admission of refrigerant into the container is terminated when the vapor pressure of refrigerant contained therein reaches a preselected level. A sensor and associated electronics are coupled to the container for determining type of refrigerant vapor in the container as a function of one or more selected properties of the refrigerant vapor, and indicating such refrigerant type to the operator. Preferably, refrigerant is admitted into the container in vapor phase by passing the refrigerant through a capillary tube, a metering orifice or a liquid refrigerant trap.

Vapor pressure within the container may be measured and indicated by a gauge or by an electrical pressure sensor. Admission of refrigerant into the container may be terminated by means of a manual valve closed by the operator when container pressure reaches the desired level, or by a solenoid valve automatically responsive to control electronics. The sensor for determining refrigerant type may comprise a temperature or pressure sensor for sensing changes in refrigerant vapor properties as heat is added to the contained refrigerant vapor. Alternatively, the sensor may take the form of a capacitance-type sensor responsive to refrigerant vapor dielectric properties, or a transmitter/receiver responsive to acoustic properties of the refrigerant vapor.

BRIEF DESCRIPTION OF THE DRAWINGS

The invention, together with additional objects, features and advantages thereof, will best be understood from the following description, the appended claims and accompanying drawings in which:

DETAIL DESCRIPTION OF PREFERRED EMBODIMENTS

Figure 1:
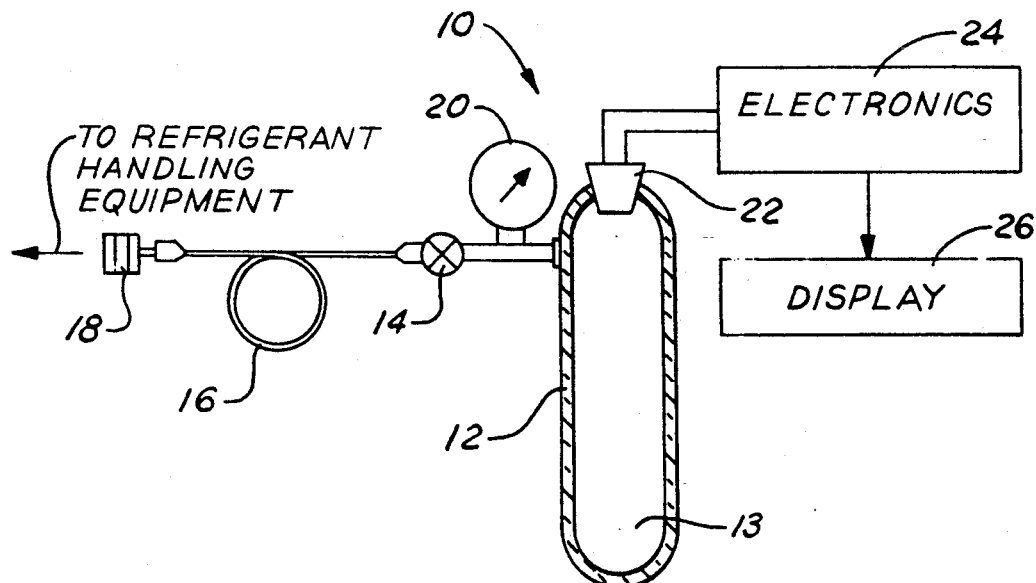
FIG. 1 is a schematic diagram of refrigerant vapor sampling and testing apparatus in accordance with one presently preferred embodiment of the invention.

FIG. 1 illustrates apparatus 10 for identify and distinguishing different refrigerant types in accordance with one presently preferred embodiment of the invention as comprising a sample container 12 having a fixed internal volume 13. Refrigerant is admitted to container 12 through a manual valve 14 and a capillary tube 16 coupled to a quick-disconnect fitting 18 of suitable type or configuration. Fitting 18 is adapted for connection to the conventional standard service fittings of refrigeration systems, with the quick-disconnect coupling disclosed in U.S. application Ser. No. 07/334,178 filed Apr. 6, 1989 and assigned to the assignee hereof, now U.S. Pat. No. 5,005,375, being of suitable albeit exemplary construction. A pressure gauge 20 is connected between valve 14 and internal volume 13 of container 12 for indicating to an operator vapor pressure of refrigerant within the container. A sensor 22 is mounted on the container and communicates with container internal volume 13. Sensor 22 provides electrical signals to the sensor electronics 24 that vary as a function of molecular weight of refrigerant vapor within container 12. Electronics 24 drive a display 26 that indicates to an operator the type of refrigerant vapor within container 12.

Figure 3:
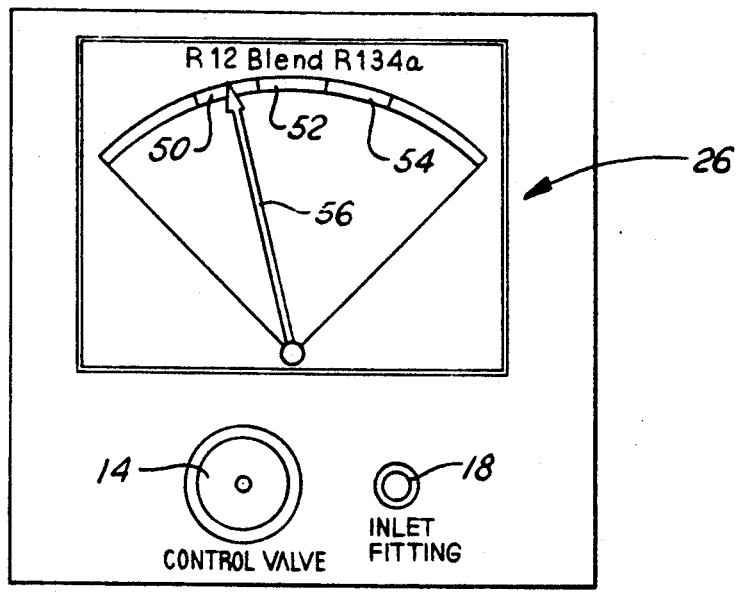
FIGS. 3-5 are elevational views of the operator display panels in three embodiments of the invention.
Figures 4, 5:
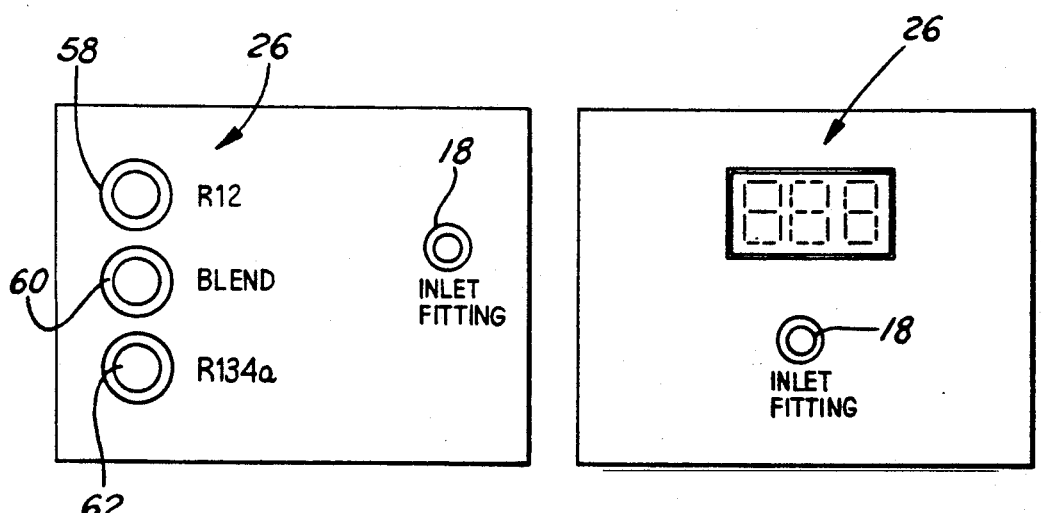

In use, fitting 18 is first coupled to a vacuum pump, and container 12, valve 14 and capillary tube 16 are evacuated. Valve 14 is then closed, and fitting 18 is coupled to the source of refrigerant to be tested, such as an automotive air conditioning system or other equipment to be serviced, or coupled to a source of fresh or purified refrigerant such as a refrigerant storage container. Valve 14 is then opened by the operator, and refrigerant is admitted into container 12. Capillary tube 16 ensures that refrigerant admitted into container 12 is in vapor phase, and slows the filling process for more precise control. When a desired test pressure of refrigerant has been reached within container 12, as indicated by gauge 20, the operator closes valve 14. Electronics 24 are then responsive to sensor 22 to determine the type of refrigerant vapor within container 12 (as will be described hereinafter), and the refrigerant type is indicated at display 26 (FIGS. 3-5).

Figure 2:
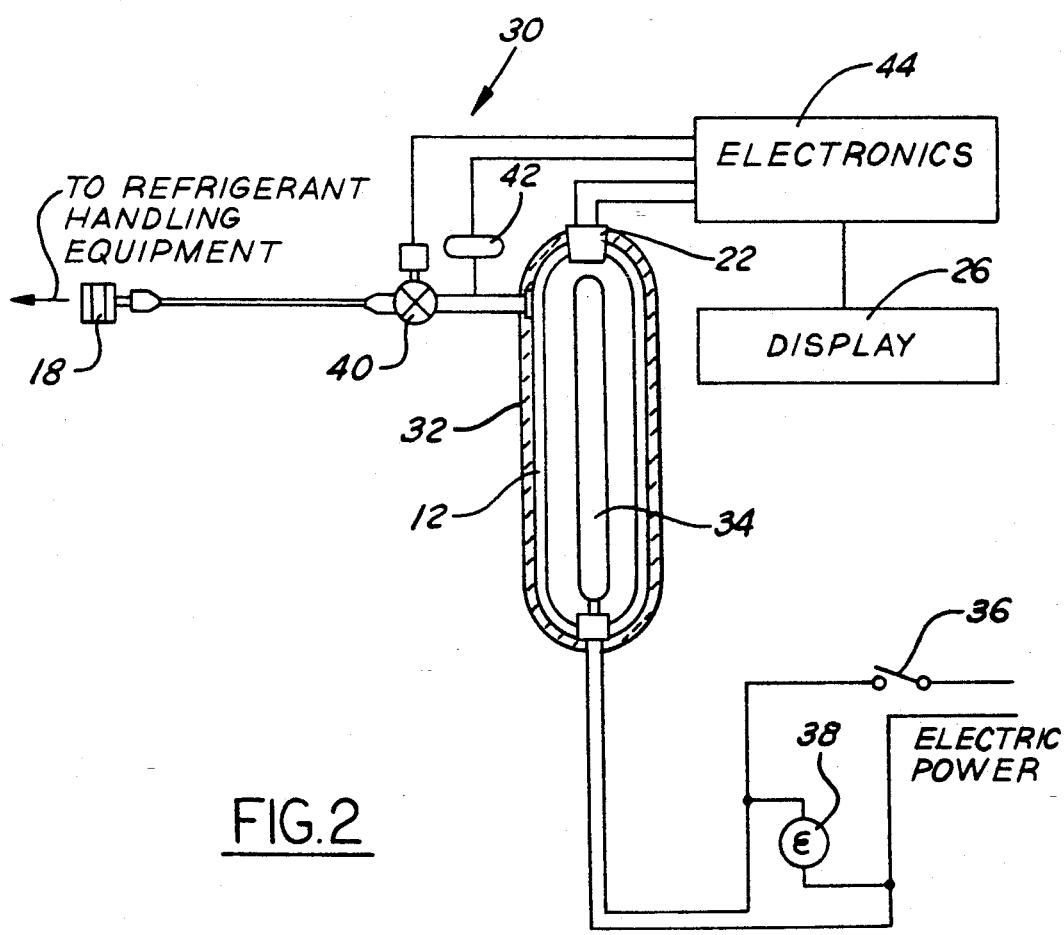
FIG. 2 is a schematic diagram of a modified embodiment of the invention.

FIG. 2 illustrates apparatus for identifying and distinguishing refrigerant types that contains a number of modifications. Container 12 is surrounded by an insulating blanket 32 and contains an electrical heating element 34 within open container volume 13. Heating element 34 is coupled to an operator switch 36 for selectively applying power to the heater, and thereby heating the refrigerant vapor within the container. A lamp 38 is connected across the power lines to the heater for indicating to the operator that power is being applied to the heater. Manual valve 14 and capillary tube 16 in the embodiment of FIG. 1 are replaced in the embodiment of FIG. 2 by a solenoid-operated metering valve 40. Gauge 20 is replaced in the embodiment of FIG. 2 by a pressure sensor 42, which provides an electrical signal to control electronics 44 indicative of refrigerant vapor pressure within container 12. Electronics 44 are responsive to the pressure signal from sensor 42 to close valve 40 when the desired refrigerant vapor pressure has been reached.

A number of techniques can be employed to determine the type of refrigerant within container 12 as a function of one or more selected properties of the refrigerant. Sensor 22 with associated electronics 24 or 44 can take a number of forms. For example, one form of the ideal gas law may be expressed as: $PV = NR_uT$, where P is absolute pressure in pounds per square foot, V is volume in cubic feet, N is pounds mass divided by molecular weight of the refrigerant, Ru is the ideal gas constant (1545 ft-lbs/lbmole°R), and T is absolute temperature (°R). If the fixed volume of container 12 is filled to a specific pressure and remains at a substantially constant controlled temperature, the only variable in the foregoing expression is the value of N. The electronics may be readily empirically calibrated to distinguish between different types of refrigerants having different molecular weights. It is also to be noted that, since absolute values are not necessary to distinguish between or among refrigerant types, it is not necessary precisely to control refrigerant vapor pressure or temperature within the container. For example, a 20° F. variation from 70° F. will result in a change in either N or P of only about three and four percent.

Another technique, for which the embodiment of FIG. 2 is particularly useful, is to determine the refrigerant type as a function of specific heat at constant volume. That is, heater 34 is energized for a predetermined time duration, and refrigerant type can then be determined as a function of heat added to the refrigerant vapor, which in turn is determined by a change in temperature or pressure of the refrigerant within the container 12. That is, the change in temperature or pressure of the refrigerant vapor within the container 12 is dependent upon the constant volume specific heat characteristics of the test refrigerant.

Sensor 22 may take a number of forms, dependent upon the technique employed for determining the refrigerant type. For example, when employing the specific heat at constant volume technique discussed immediately above, sensor 22 may comprise either a temperature sensor or a pressure sensor for providing electrical signals to electronics 44 (FIG. 2) as a function of temperature or pressure of the refrigerant vapor within container 12. Alternatively, sensor 22 may take the form of a capacitance-type sensor for determining refrigerant type as a function of refrigerant vapor dielectric properties, either in the constant temperature embodiment of FIG. 1 or in the varying temperature embodiment of FIG. 2. Sensor 22, in either of the embodiments of FIGS. 1 or 2, may comprise a transmitter/receiver for determining refrigerant type as a function of acoustic properties thereof by means of a change in velocity or phase angle of acoustic waves propagated within the container as a function of a change in density, temperature or pressure of the refrigerant vapor. In all of these alternative embodiments, it is important to note that absolute precision is not needed to distinguish between different types of refrigerant.

FIGS. 3-5 illustrate three different configurations for display 26 and the associated operator panel. In FIG. 3, display 26 takes the form an analog meter having separate zones 50, 52, 54 along the meter display with associated alphanumeric indicia for indicating the presence of R12, blend or R134a refrigerant, for example. Thus, in this embodiment, current applied to the meter varies as a function of refrigerant type to place the needle 56 of the meter in the associated display zone. In the embodiment of FIG. 4, display 26 takes the form of three lamps 58, 60, 62 with adjacent alphanumeric indicia for indicating R12, blend or R134a refrigerant. In the embodiment of the FIG. 4, the display drive electronics thus determine the refrigerant type and energize the appropriate lamp. In the embodiment of FIG. 5, display 26 takes the form of a digital readout, and the display drive electronics determine the type of refrigerant and energize the digital display accordingly. It is also to be noted that the operator panel in the embodiment of FIG. 3 includes a handle for manual control valve 14 (FIG. 1), whereas the embodiments of FIGS. 4 and 5 contemplate automatic closure of solenoid valve 40 (FIG. 2) and therefore include no such manual valve handle.

We claim:

1. Apparatus for identifying and distinguishing between at least two different types of refrigerant comprising:

a closed container of fixed internal volume, refrigerant-admitting means for selectively admitting refrigerant into said closed container, means for measuring vapor pressure of refrigerant in said closed container, means for terminating admission of refrigerant into said closed container when vapor pressure therein reaches a preselected level, sensing means for sensing type of refrigerant vapor in said closed container as a function of one or more selected properties thereof, and means responsive to said sensing means for indicating type of refrigerant in said closed container.

2. The apparatus set forth in claim 1 wherein said refrigerant-admitting means includes refrigerant-vaporizing means for vaporizing refrigerant entering said closed container.

3. The apparatus set forth in claim 2 wherein said refrigerant-vaporizing means comprises a capillary tube.

4. The apparatus set forth in claim 2 wherein said refrigerant-vaporizing means comprises a metering orifice.

5. The apparatus set forth in claim 4 wherein said means for terminating admission of refrigerant comprises a metering valve that includes said metering orifice.

6. The apparatus set forth in claim 5 wherein said metering valve comprises a manual valve.

7. The apparatus set forth in claim 6 wherein said means for measuring vapor pressure comprises a pressure gauge.

8. The apparatus set forth in claim 5 wherein said metering valve comprises a solenoid valve, wherein said means for measuring vapor pressure comprises a pressure sensor coupled to said closed container for providing an electrical signal as a function of refrigerant vapor pressure therewithin, and wherein said means for terminating admission of refrigerant further comprises electronic control means responsive to said electrical signal for closing said solenoid valve.

9. The apparatus set forth in claim 2 wherein said refrigerant-vaporizing means comprises a liquid refrigerant trap connected between said refrigerant admitting means and said closed container.

10. The apparatus set forth in claim 1 wherein said means for measuring vapor pressure comprises a gauge coupled to said closed container for indicating to an operator vapor pressure of refrigerant in said closed container.

11. The apparatus set forth in claim 10 wherein said means for terminating admission of refrigerant to said closed container comprises a manual valve.

12. The apparatus set forth in claim 1 wherein said means for measuring vapor pressure in said closed container comprises a pressure sensor for providing an electrical signal as a function of such vapor pressure.

13. The apparatus set forth in claim 12 wherein said means for terminating admission of refrigerant comprises a solenoid valve, and electronic control means coupled to said solenoid valve and responsive to said electrical signal for automatically closing said solenoid valve when vapor pressure of refrigerant in said closed container reaches said preselected level.

14. The apparatus set forth in claim 1 wherein said sensing means comprises a capacitance sensor and means responsive to dielectric properties of refrigerant vapor in said closed container for determining refrigerant type.

15. The apparatus set forth in claim 1 wherein said sensing means comprises acoustic transmitting/receiving means and means responsive to acoustic properties of refrigerant vapor in said closed container for determining refrigerant type.

16. The apparatus set forth in claim 1 wherein said sensing means comprises a temperature sensor and means responsive to thermal properties of refrigerant vapor within said closed container for determining refrigerant type.

17. The apparatus set forth in claim 16 further comprising heat-adding means for adding heat to refrigerant vapor within said closed container, and wherein said means responsive to said thermal properties comprises means responsive to changes in temperature of said refrigerant vapor for determining said refrigerant type as a function of specific heat of said refrigerant vapor.

18. The apparatus set forth in claim 17 wherein said heat-adding means comprises an electrical heater positioned within said closed container and means for selectively applying electrical power to said electrical heater.

19. The apparatus set forth in claim 18 further comprising insulating means surrounding said closed container.

20. The apparatus set forth in claim 1 further comprising heat-adding means for adding heat to refrigerant vapor within said closed container, and wherein said sensing means comprises a pressure sensor and means responsive to changes in pressure of refrigerant vapor within said closed container for determining said refrigerant type as a function of heat added thereto.

21. The apparatus set forth in claim 20 wherein said heat-adding means comprises an electrical heater positioned within said closed container and means for selectively applying electrical power to said electrical heater.

22. The apparatus set forth in claim 21 further comprising insulating means surrounding said closed container.

23. The apparatus set forth in claim 1 further comprising heat-adding means for adding heat to refrigerant vapor within said closed container, and wherein said sensing means comprises means responsive to changes in properties of said refrigerant vapor for determining said refrigerant type.

24. The apparatus set forth in claim 23 wherein said heat-adding means comprises an electrical heater positioned within said closed container and means for selectively applying electrical power to said electrical heater.

25. The apparatus set forth in claim 24 further comprising insulating means surrounding said closed container.

26. The apparatus set forth in claim 1 further comprising insulating means surrounding said closed container.

* * * * *